(12) United States Patent
Wiksell et al.

(10) Patent No.: US 7,871,383 B2
(45) Date of Patent: Jan. 18, 2011

(54) ARRANGEMENT FOR CELL SAMPLING

(75) Inventors: Hans Wiksell, Täby (SE); Gert Auer, Solna (SE); Vilhelm Ekstrand, Nacka (SE); Peter Harge, Saltsjöbaden (SE)

(73) Assignee: VibraTech AB, Stockholm (SE)

( * ) Notice: Subject to any disclaimer, the term of this patent is extended or adjusted under 35 U.S.C. 154(b) by 179 days.

(21) Appl. No.: 11/663,723

(22) PCT Filed: Sep. 21, 2005

(86) PCT No.: PCT/SE2005/001386
§ 371 (c)(1),
(2), (4) Date: May 22, 2007

(87) PCT Pub. No.: WO2006/036108
PCT Pub. Date: Apr. 6, 2006

(65) Prior Publication Data
US 2008/0058671 A1 Mar. 6, 2008

Related U.S. Application Data

(60) Provisional application No. 60/612,787, filed on Sep. 27, 2004.

(30) Foreign Application Priority Data
Sep. 27, 2004 (EP) .................. 04104693

(51) Int. Cl.
*A61B 10/00* (2006.01)
(52) U.S. Cl. ..................................... 600/566
(58) Field of Classification Search ......... 600/562–568, 600/570, 571; 606/28, 41, 181–185, 178; 604/22; 173/48, 109, 205; 408/17
See application file for complete search history.

(56) References Cited

U.S. PATENT DOCUMENTS

| | | | |
|---|---|---|---|
| 3,834,468 A * | 9/1974 | Hettich et al. ................. 173/48 |
| 4,605,011 A | 8/1986 | Naslund | |
| 6,086,543 A * | 7/2000 | Anderson et al. ........... 600/567 |
| 6,086,544 A | 7/2000 | Hibner et al. | |
| 6,210,421 B1 * | 4/2001 | Bocker et al. ............... 606/182 |
| 6,402,701 B1 | 6/2002 | Kaplan et al. | |
| 6,432,065 B1 | 8/2002 | Burdorff et al. | |

(Continued)

FOREIGN PATENT DOCUMENTS

EP 1 428 477 6/2004

(Continued)

*Primary Examiner*—Max Hindenburg
*Assistant Examiner*—Brian Szmal
(74) *Attorney, Agent, or Firm*—Young & Thompson

(57) ABSTRACT

An arrangement for taking a sample of cells from a suspicious lesion or a tumor with the so called fine needle aspiration technique, provides a good penetration of tumors, especially small and/or hard fibrous tumors, and in the meantime yielding an increased amount of cells in the sample, by applying a longitudinal movement to the needle when the needle is penetrating the tumor and by applying both a rotational and a longitudinal movement to the needle when the needle is positioned inside the tumor. The arrangement is further provided with heat generating elements in order to apply a short pulse of heat to the needle in order to lower the risk for the tumor to spread.

10 Claims, 3 Drawing Sheets

U.S. PATENT DOCUMENTS

| | | |
|---|---|---|
| 6,592,530 B1 | 7/2003 | Farhadi |
| 6,689,072 B2 | 2/2004 | Kaplan et al. |
| 6,702,761 B1 | 3/2004 | Damadian et al. |
| 6,770,070 B1 * | 8/2004 | Balbierz .................. 606/41 |
| 2002/0055689 A1 | 5/2002 | Kaplan et al. |
| 2002/0077565 A1 | 6/2002 | Burdorff et al. |
| 2004/0097920 A1 | 5/2004 | Desinger |
| 2004/0162505 A1 | 8/2004 | Kaplan et al. |
| 2005/0054971 A1 * | 3/2005 | Steen et al. .................. 604/22 |

FOREIGN PATENT DOCUMENTS

| | | |
|---|---|---|
| JP | 2000316867 | 11/2000 |
| JP | 2001517470 | 10/2001 |
| JP | 2003533325 | 11/2003 |
| JP | 2004154296 | 6/2004 |
| WO | 99/15079 | 4/1999 |
| WO | 00/56208 | 9/2000 |
| WO | 0056208 | 9/2000 |

* cited by examiner

ARRANGEMENT FOR CELL SAMPLING

TECHNICAL FIELD

The present invention relates to an arrangement for taking a sample of cells from a suspicious lesion or a tumour with the so called fine needle aspiration (FNA) technique, which arrangement provides a good penetration of tumours, especially small and/or hard fibrous tumours, and in the meantime yielding an increased amount of cells in the sample in comparison with prior art arrangements. The inventive arrangement also comprises a sample kit and the present invention also relates to a method for taking samples of cells from tumours which brings about the above mentioned advantages.

BACKGROUND ART

Many women in the western world faces the prospect of breast cancer and when it comes to tumour therapy it is important that a high quality diagnosis of the tumour is made. The diagnosis is often based on morphological findings and there are today two main methods for morphological diagnosis of breast lesions i.e. histopathological examination of surgical or punch biopsies and cytopathological examination of fine needle aspirates.

In punch or core biopsy, a tissue sample of the lesion is removed, for instance with the use of a coarse punching biopsy-needle, which sample is subsequently examined histologically. This procedure is generally associated with side-effects e.g. extensive local bleeding and pain. The total expenses for each diagnosed lesion are high in comparison with the cost associated with the corresponding cytological diagnosis.

With cytological diagnosis, single cells and small cells complexes are aspirated from the lesion with the aid of a fine needle in which low pressure is created during the sampling process. Due to the lower adhesion between tumour cells than between healthy cells, the tumour cell concentration in the sample is enriched. Subsequent to taking the cell sample, the cell material is examined by e.g. ejecting them onto a glass slide, where they are smeared, fixed, stained and examined cytomorphologically. Ongoing advances in genetics and functional genomics suggest that a completely objective molecular diagnostic procedure in single cells from fine needle aspirates will be available in a near future.

In the recent years it has been possible to detect smaller and smaller tumours, for instance through the technical development of screening mammography and ultrasound diagnostic scanning. It is not unusual to detect tumours which are in the size of just a few millimetres. Especially these small tumours but also tumours of sizes 10-20 mm in diameter are frequently non-palpable and undergo anatomical distortion when hit by the needle. The reason is that the glandular breast tissue is surrounded by a loose fatty and connective tissue, which makes it difficult to correctly position and move the needle into the tumour and the problem aggravates if the tumour is hard or fibrous, which is most often the case. Thus, the insertion of above all core biopsy needles but also fine needles into the tumour is often difficult or even impossible.

From U.S. Pat. No. 4,605,011 (J. NÄSLUND) it is known to take samples of cells from small tumours with the aid of a fine-needle puncturing technique. The patent specification describes a cell sampling apparatus with a removable connected syringe provided with a cannula which can be driven with an oscillating, reciprocatory movement into the tumour in order to facilitate the insertion of the cannula into said tumour. Said apparatus is provided with means for creating reduced pressure in the cannula for driving a cell sample thereinto.

Cell sampling from tumours of small sizes (2-10 mm in diameter) is frequently associated with major sampling problems resulting in non-representative or sparse cellular material. This is a decisive drawback of this patient-friendly method because of the rapid increase of the total number of breast tumours below the size of 10 mm detected by means of mammography and ultrasound screening.

WO 00/56208 describes a fine needle biopsy device for extracting tissue from the body predominantly in suspected cases of breast cancer. The device causes a fine needle, which is attached to the device to reciprocate and/or rotate at the same time causing tissue to enter the needle, optionally with the aid of suction for aspiration of the tissue sample. The frequency used for the reciprocating movement is in the range of 10-20 Hz and moreover, the reciprocating and the rotational movement, respectively, may not be changed independently.

The fact that the adhesion between tumour cells is less than between healthy cells, causes another problem with the cytological aspiration technique. The insertion of the needle into the tumour, followed by the withdrawal of the "contaminated" needle is believed to cause a certain risk of tumour cells to spread in the needle channel, which might give rise to a local spread of tumour cells (seeding).

Another issue in the cytological aspiration technique to attend is the prevention of filling the needle with material from tissue surrounding the tumour when the needle is inserted into the breast.

Still another issue to attend is the cell sampling of cystic tumours. If a lesion is cystic, the obtained sample volume is increased. However, the cell material in the sample will be diluted. At the present the sample may for instance undergo centrifugation subsequent to the sampling procedure in order to retrieve the cells to be examined cytomorphologically. This is a rather labour intensive and time consuming procedure and often the retrieved cell concentration is low.

The cytological aspiration technique for diagnosis of tumours is however a very promising technique since the side effects are lenient and few, especially when objective molecular diagnostic methods will be available. For instance, the technique does not cause any severe internal bleeding or major pain, thus providing a great benefit for the patient and in the end lowered costs for the society. Moreover, cytological aspiration is also associated with a relatively low success rate for physicians without considerable experience. Consequently, there is a need for standardisation and improvements of said technique, such as in a standardised way providing a good penetration and low anatomical distortion of small tumours, in the meantime yielding an increase of the amount of cells in the sample taken to ensure a high quality diagnosis. There is also a need for a lowering of the risk for the tumour to spread when a cell sample is taken from a tumour, for instance a histologically poorly differentiated highly malignant tumour.

Further there is a need for an arrangement that in an effective way prevents the needle to be filled with unwanted material during the insertion of the needle into the breast and into the tumour. Moreover, there is a need for an arrangement that in an effective way increases the cell concentration when taking a cell sample from for instance a cystic tumour, which also provides for a faster and less labour intensive procedure.

DISCLOSURE OF THE INVENTION

Thus, the object of the present invention is to provide an arrangement for taking a sample of cells from a lesion with the cytological aspiration technique, which provides a good penetration and low anatomical distortion or dislocation of tumours, especially small and/or hard fibrous tumours. Said arrangement yields an increased amount of cells in the sample in comparison with prior art arrangements.

This object is achieved by an arrangement according to the preambles of the independent claims and provided by the features according to the characteristic portions of the independent claims.

Another object of the inventive arrangement is to lower the risk for the tumour to spread when taking a cell sample from said tumour.

Moreover, the present invention provides an arrangement for avoiding unwanted material to be brought into the needle from tissue surrounding it when the needle is inserted into the breast.

The present inventions also provides for an arrangement that in an effective way increases the cell concentration when taking a cell sample from for instance a cystic tumour, which also provides for a faster and less labour intensive procedure.

Furthermore, the inventive arrangement provides means that enables a more standardised sampling procedure.

MODE(S) FOR CARRYING OUT THE INVENTION

Figure 1:
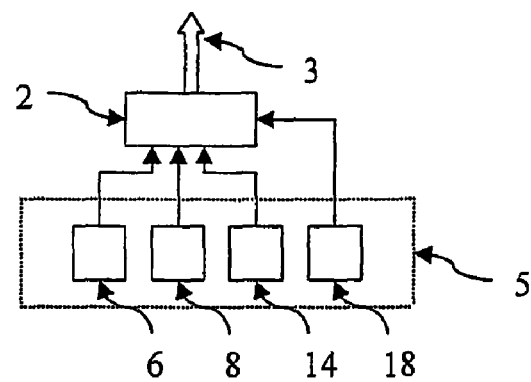
FIG. 1 schematically shows the inventive arrangement in the preferred embodiment.
Figure 2:
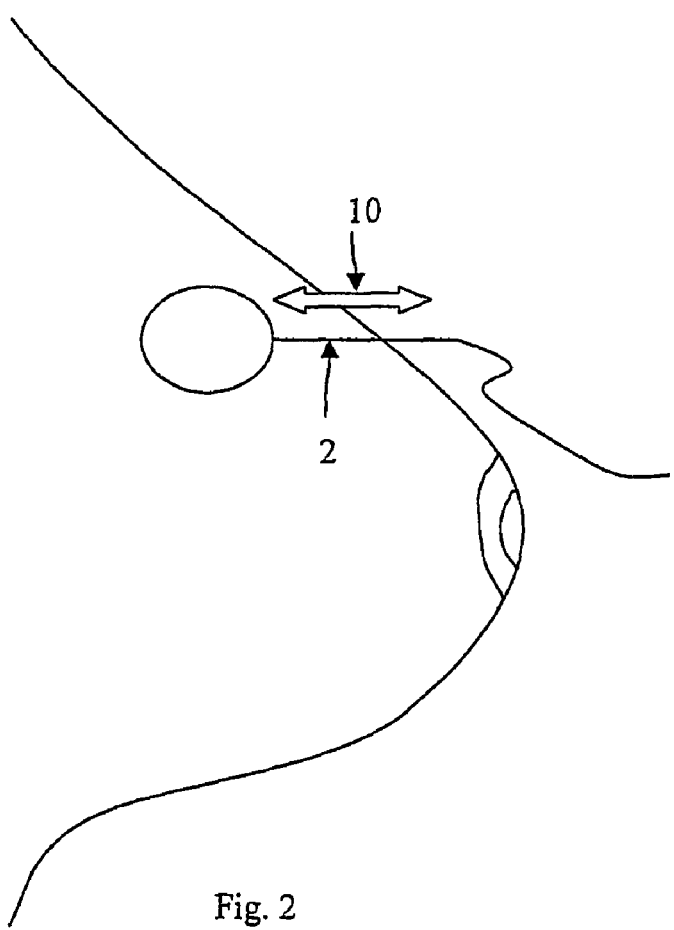
FIG. 2 shows the invention in a first stage of a cell sampling procedure.
Figure 3:
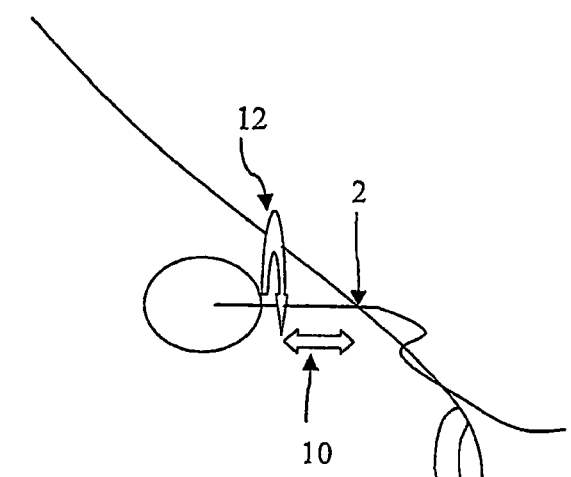
FIG. 3 shows the invention in a second stage of the cell sampling procedure.
Figure 4:
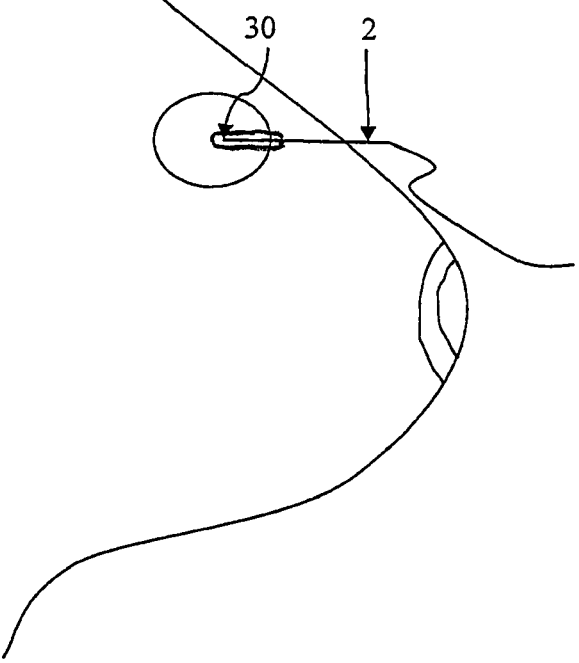
FIG. 4 shows the invention in a third and preferred stage of the cell sampling procedure.
Figure 5:
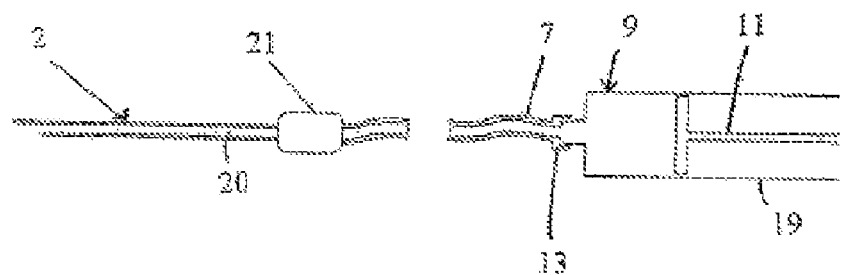
FIG. 5 schematically shows a sample kit of the inventive arrangement in a first preferred embodiment (not to scale)

As seen from FIG. 1, the arrangement of the present invention comprises a fine hollow needle 2 provided with a through-going aspiration channel 20 (FIG. 5) that is communicating with a set of means 5 that are adapted to set the needle 2 in different modes of action 3. Said set of means 5 comprises a longitudinal movement means 6 that is adapted to apply an oscillating longitudinal movement 10 (FIG. 2) to the needle 2, a rotational movement means 8 that is adapted to apply a rotational movement 12 (FIG. 3) to the needle 2 and a pressure regulating means 14 that is adapted to create a reduced pressure as well as an over pressure in said aspiration channel 20 of the needle 2. According to a preferred embodiment, said set of means 5 comprises a heat generating means 18 that is adapted to apply heat generating energy to the needle 2. The inventive arrangement is provided with control means (not shown) with which the operator of the arrangement is able to control the set of means 5 and thus the different modes of action 3 of the needle 2. The control means enables applying suitable and standardised values of parameters that are important for the cell sampling procedure, to the set of means 5.

The inventive arrangement will now be described by means of a preferred cell sampling procedure from a breast lesion.

Before the cell sampling procedure the position and size of the lesion is localized by means of for instance x-ray, ultrasound or manual palpation. Depending on the above mentioned factors, as well as for instance the condition of the patient, the operator of the arrangement, i.e. for instance the physician responsible for the cell sampling procedure, chooses a needle 2 of suitable dimensions and type for the procedure. Typically the needle 2 has an external diameter in the range of 0.4-1.0 mm and a length of 15-100 mm. The needle 2 is preferably a disposable article, provided together with a sample kit, in a first embodiment also including a disposable hose 7 and a disposable pressure-pump devise 9 (FIG. 5) (see further discussion below). The sample kit, in the first as well as in the second embodiment (described in further detail below), is preferably provided pre-sterilized and in a suitable dateline marked packaging, and easily fitted with the arrangement by the operator. Thus, the inventive arrangement is preferably adapted to be compatible with needles of different dimensions and thus the set of means 5 are preferably adapted to apply suitable parameter values to the needle 2 depending on the needle dimension, lesion size, sampling procedure etc.

After fitting of a suitable needle 2 with the arrangement, i.e. fitting of a suitable sample kit, the operator inserts the needle into the breast towards the (suspicious) tumour. Preferably, when the needle is about to penetrate the tumour (FIG. 2), the operator applies an oscillating longitudinal movement 10 to the needle 2 by the use of the longitudinal movement means 6. Depending on for instance the dimensions of the needle 2 and the size, condition and localization of the lesion, the operator is free to choose a suitable frequency and amplitude that is to be applied to the needle 2. Preferably the non-elastic frequency is in the range of 30-300 Hz and the amplitude in the range of 0-4 mm. Longitudinal oscillation 10 of the needle 2 with suitable frequency and amplitude will due to it's acceleration component effectively penetrate even small and hard tumours. The inventors have in fact discovered that the resistance at penetration may be reduced by as much as ten times when a frequency of 250 Hz is applied. The penetration force is decreasing with increasing frequency and amplitude and the acceleration forces increases with the parameters.

Preferably, the procedure is monitored by means of x-ray, ultrasound or precision palpation (not shown), so that the operator may view the position of the needle 2 in relation to the lesion.

When the needle 2 is correctly positioned inside the lesion, the operator, in a second stage of the cell sampling procedure, applies a rotational movement 12 to the needle 2. The function of the rotating needle tip is to enhance the low adhesion-related cell concentration of the cell material inside the lesion, since loosen up the cells by means of mechanical "forced cutting", effectively increases the amount of cell sample, even from very small tumours. The longitudinal movement 10 of the needle 2 when the needle 2 is positioned inside the lesion, is preferably a slower motion with an amplitude that is adapted according to for instance the lesion size and shape. The effect of the longitudinal movement 10 in the second stage of the cell sampling procedure is that the needle 2 is brought into contact with a larger volume of the lesion, preferably belonging to the entire lesion. The longitudinal movement 10 and the rotational movement 12 are independent movements and may be varied independently of one another during the entire cell sampling procedure in order to achieve optimal performance conditions. The longitudinal movement 10 of the needle 2 in the second stage of the cell sampling procedure is optional and may thus be left out.

The time needed for the needle 2 to be in the rotational mode 12 is dependent on for instance the tumour size and condition but is generally in the range of a few seconds and a typical number of revolutions per minute (rpm) for the needle tip is in the range of 10-1500 rpm. If no vacuum tight rotational coupling (not shown) is used in the sample kit, one might need to alternate the rotation direction in order to avoid twining of the hose.

During the second stage of the cell sampling procedure, i.e. when the needle 2 is positioned inside the lesion while in the rotational mode 12 and preferably also in the longitudinal mode 10, the needle 2 is also set in a reduced pressure mode by applying a reduced pressure to the aspiration channel 20 of the needle 2 by use of the pressure regulating means 14, such that cells from the lesion is aspirated into the channel 20. A suitable applied reduced pressure is for instance approximately—800 mBar. At the end of the second stage of the cell sampling procedure the pressure in the needle 2 is equalized.

In a preferred embodiment, the aspiration channel 20 is filled with a liquid (26) (FIG. 5), preferably a sterile isotone NaCl solution. The filling liquid functions as a "hydraulic mandarin" that prevents that the needle 2 is filled with unwanted material from tissue surrounding the lesion during the insertion of needle 2 into the breast and into the tumour. When the aspiration channel 20 is provided with filling liquid, said liquid is drawn into for instance the hose 7, or into the pressure pump depending on the embodiment of the sampling kit, when applying the reduced pressure, whereupon the cells from the lesion is aspirated into the aspiration channel 20.

Alternatively the needle 2 may, for the same reason as mentioned above, be provided with a metal mandarin instead of a hydraulic mandarin, designed in order to fit inside the hollow part of the needle and adopted to be functional with the inventive arrangement.

According to still another preferred embodiment, the needle 2 is also connected to the heat generating means 18 that is adapted to apply energy to the needle 2 in order to heat tissue in the immediate surroundings of said needle 2 in a heat generating mode. Preferably the heat generating means 18 comprises a low impedance radio frequency (RF) generating source, applying a voltage between the needle and a indifferent counter electrode (not shown) applied to a suitable outer surface of the patient, for instance on the patient's back. All in accordance with a technique generally known as the monopolar regime used in for example radio frequency ablation or diathermi. After the cell sample has been aspirated into the needle 2, or during said second stage of the procedure, the operator applies in a preferred third stage of the procedure, at least one short pulse, preferably in the duration range of 1 ms-2 s, of RF-energy, preferably in the range of 3-2000 W, between the needle 2 and the counter-electrode, such that a pulse of heat 30 denaturises tissues in a small cylindrical tissue-volume shape surrounding the needle 2. The temperature of the generated heat 30 is preferably over 60° C., more preferably 80° C., and most preferred 90° C. The generated heat 30 effectively denaturises cells in the very near surrounding of the needle 2, preferably in a radius of for instance not greater than approximately 0.1 mm from the needle 2, thus preventing smeared tumour cells in the aspiration channel 20 to survive. Due to the Faradays-cage effect in the hollow needle 2 and due to the short heating time, the heat 30 generated around the needle 2, does not thermally damage the cell-sample inside the needle 2. According to said preferred embodiment of the present invention, the needle surface is preferably provided with an insulating material (not shown) at the upper part of the needle 2 that is in direct contact with the naked skin, such that heat damage of the skin is effectively avoided. Subsequent to the heat generating mode, the needle 2 may in a final stage of the procedure be withdrawn from the breast. Alternatively, the needle 2 is withdrawn from the breast after completion of the second stage of the cell sampling procedure.

Once the needle 2 is withdrawn from the body, the cell sample is removed from the aspiration channel 20 of the needle 2 with a short pulse of over pressure by means of for instance the pressure regulating means 14 and may be transferred for further preparations. Due to risk of inducing air embolism said final overpressure stage is prevented from occurring while the needle 2 is still positioned inside the body, for instance by the use of impedance measurements of the needle 2, i.e. a block-function or the like, that prevents over pressure to be applied when the needle is positioned inside the body. To increase the cell concentration in the cell sample when a sample is to be taken from for instance a cystic tumour, a filter (not shown), preferably a micro-filter, is removably incorporated in the needle compartment which effectively collects the cells of the diluted sample of the tumour. Subsequently to taking the sample, and after the needle 2 has been removed from the breast, the filter is removed and the cells may be fixed, stained and examined cytomorphologically, possibly directly on the filter. This makes the procedure faster because centrifugation of the sampling material becomes superfluous.

The above mentioned sample kit preferably comprises in a first embodiment the hollow needle 2, a hose 7, preferably made of a pyrogen-free flexible material such as for instance silicone rubber or PVC, as well as a pressure-pump device 9, which will be described in further detail below. The needle 2 is to be fitted at the first end of the hose 7, via a needle coupling adapter means 21, and the pressure-pump device 9 is incorporated in the second end of said hose 7. The hose 7 is preferably provided with valve-function 13, or alternatively the needle 2 is provided with a valve function. The needle coupling adapter means 21 is adapted to be easily fitted in a light-weight, preferably pen-shaped hand-piece 25 that is designed to transfer the movements 10, 12 to the needle as well as designed to electrically connect the needle 2 to measurement devices and the like. The hand-piece 25 is of a suitable size and preferably provided with a light-emitting diode or the like (not shown). The hand-piece 25 is preferably insulated in accordance with medical standards as the EN 60.601.1, CE and others, so that the patient leakage current (PLC) will be Cardiac Floating (CF)=less than 10 mA frequency weighted, as well as Earth Leakage Current (ELC) within appropriate limits.

As mentioned above, the sample kit is preferably provided as a sterilized consumable article and easily fitted with the arrangement.

The pressure-pump device 9 is provided with a piston 11 communicating with the pressure regulating means 14, which piston 11 is adapted to move inside a cylinder 19 by means of the pressure regulating means 14. Since the pressure-pump device 9 is connected to the aspiration channel 20 via the hose 7, the movement of the piston 11 thus creates reduced pressure or overpressure, respectively, in the aspiration channel 20 of the needle 2. For instance, in the initial phase of the reduced pressure mode, the piston 11 is positioned at a first end of the cylinder 19, whereupon said piston 11 is moved by means of the pressure regulating means 14 towards a second end of said cylinder 19, creating a reduced pressure in the channel 20, that aspirates a cell sample into the needle, and if the needle 2 is filled with a liquid, draws said liquid into the hose 7. Subsequent to the reduced pressure mode, the pressure regulating means 14 releases the piston 11 whereupon pressure equilibrium is established in the aspiration channel 20 by means of the pneumatic under pressure, i.e. dangerous air-injection in to the body is thus effectively prevented. During the overpressure mode in the final stage of the cell sampling procedure, the piston 11 is initially positioned at the second end of the cylinder 19 whereupon the piston 11 by means of the pressure regulating 14 is moved towards the first end of the cylinder 19, creating an overpressure in the aspiration channel 20 and thereby ejecting the lesion tissue sample.

Figure 6:
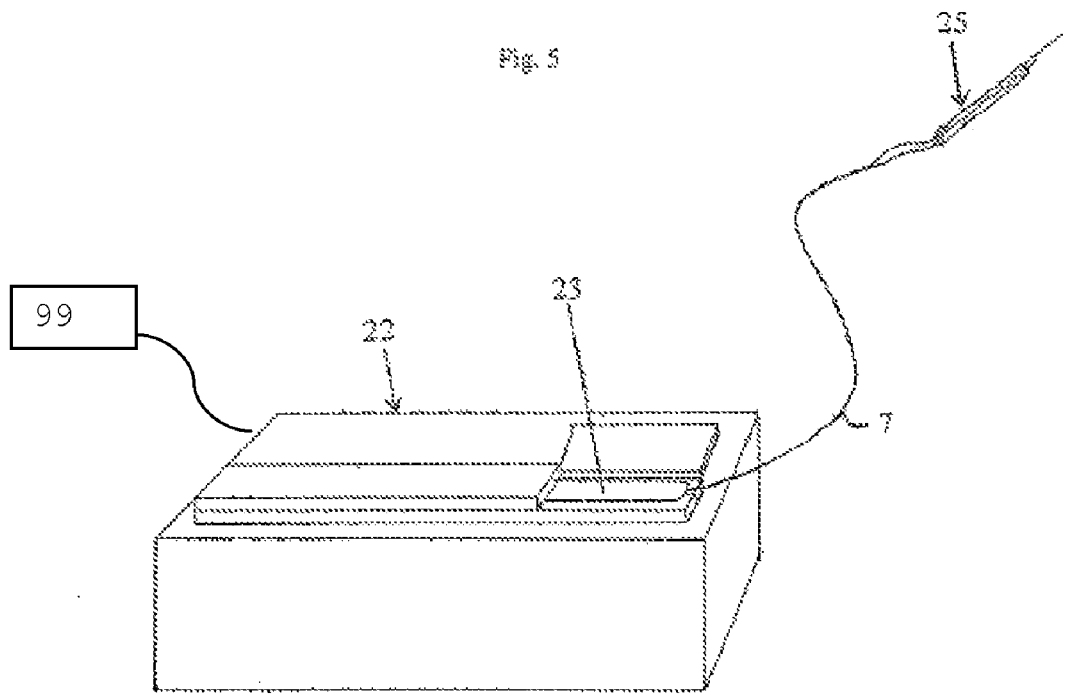
FIG. 6 shows a preferred embodiment of the console adapted to house parts of the sample kit of FIG. 5.

The pressure pump device 9 is preferably adapted to be fitted in the console 22 in a recess 23 (FIG. 6). Preferably the console 22 operates the pressure-pump device 9 with for instance a motor or the like (not shown). Alternatively, said motor or the like may be provided in the hand piece 25.

The console 22 preferably comprises the control means, which preferably is computerised and provided with programming means, i.e. the console 22 is preferably provided with a computer 99, which controls input and output signals to ensure safe operations etc. The control means are preferably programmed to sense the presence of a sample kit in the arrangement, if said sample kit is installed correctly in the console 22 and in the hand-piece 25 and moreover, if the sterilised sample kit has been exchanged since the previous cell sampling procedure, i.e. since the treatment of the previous patient. Thus, the control means is adapted to indicate to the operator, e.g. by an optical or visual signal, that the arrangement is ready for use or if some error is detected. Preferably all the inserting and sampling parameters as well as the current stage of the procedure is displayed in order to give the operator appropriate feed-back during the procedure. In order to increase safety and improve functions, various measurements is automatically made by using electric low level signals etc., such as for instance checking the electric impedance between the needle 2 and the indifferent electrode.

Preferably the inventive arrangement is provided with a programmable control unit, preferably in the console 22. The control unit enables the operator to control and monitor the different set of means 5, for instance through sets of regulators and displays on the control unit, or alternatively through buttons on the hand-piece 25. In order to provide a more standardised cell sampling procedure the programming means preferably also allows the operator to pre-program the cell sampling procedure. That is, depending on for instance the nature of the lesion to be diagnosed and the needle in use etc., to in advance choose suitable parameters for the complete cell sampling procedure. Said parameters may be stored as default values so that the operator of the arrangement will be able to choose between certain pre-programmed cell-sampling procedures. However, the operator may at all times change optional values of parameters, if so needed. Said parameters are for instance the time lengths of the different modes, amplitude and frequency of the longitudinal movements, revolutions per minute of the rotational movement, angle velocity of the rotation etc.

It is preferred that the control means comprises foot pedals by means of which some or all of said means are maneuverable, the advantage being that the operator can have his hands etc. free to insert the needle 2 and handle the patient. Alternatively the console 22 may be provided with a touch-screen to manoeuvre said means, said touch-screen may also give vital information during the sampling process. Yet another alternative is that said means are maneuverable with buttons on the hand-piece.

In a second cord-less embodiment of the sample kit, the hand-piece 25 comprises the pressure pump device 9, the control unit and the control means as described above, as well as a rechargeable electric energy supply means.

In this embodiment the hand-piece is fully separated from the console i.e. no cords or hoses connecting the two. The pressure-pump device 9 and the energy supply means, are pre-charged using for instance an under pressure-reservoir (described below) and rechargeable accumulators, respectively, via the console.

In this cord-less embodiment, the pressure-pump device 9 is preferably provided with a piston 11 which is adapted to move inside a cylinder 19, as described above. The pressure reservoir is established in the pressure pump device, while the hand-piece is placed in the console, by moving the piston 11 to the second end of said cylinder 19 by means of a mechanical actuator or an under pressure source in the console and then lock the piston in this position, while the valve is closed. Under pressure can then be provided to the needle when the hand-piece is removed from the console, by opening the valve during the initiation of the sampling phase. To depressurise, the piston locking means is released. Prior to the overpressure phase, the hand-piece is preferably put back into the console. This is in order to establish safety means that prevents the overpressure phase to occur while the needle still being inside the human body, i.e. the overpressure phase can not be initiated unless the hand-piece is placed in the console.

In this second cord-less embodiment of the sample kit, the components being consumable articles and thus being part of the sample kit, is the hollow needle 2, the coupling adapter means 21, the pressure-pump device 9 and alternatively a hose between the needle and the pressure-pump device. Unless nothing else is described above in connection with the second embodiment of the sample kit, said second embodiment is adapted to have the same functions and provides for the same advantages as described above in connection with the first embodiment of the sample kit, with the control unit and the control means being comprised in the hand-piece.

Alternatively, the pressure pump device 9, in any of the embodiments, can be provided with an air tight chamber (not shown), including a chamber valve in which an inflatable membrane is placed as sterility barrier. Only the membrane is part of the sample kit and connected to the hose, i.e. the pressure pump device can be reused and thus, do not form a part of the sample kit. The pressure reservoir is charged in the console by creating under pressure in the chamber and closing the chamber valve. Under pressure is provided to the needle by opening the valve on the hose or the coupling adapter means, during the sampling phase. By opening the chamber-valve the needle is depressurised. During the over pressure phase the hand-piece is placed in the console and the chamber is pressurised with the means in the console. The procedure is otherwise the same as in the previous embodiment.

As an alternative the under pressure establishing means can be replaced by a cavity (not shown), preferably made of plastic and provided as a sterilized consumable article, which is mounted for instance in the cylinder 19 under spring load such that the cavity wants to expand. When the spring load on the cavity is reduced, under pressure is applied to the hollow part of the needle 2. Likewise, when external pressure is applied to the cavity, for instance by means provided in the console, over pressure is applied to the hollow part of the needle.

In all embodiments described above, the over and under pressure phases can be performed in a predetermined pulsed regime by means of the pressure regulating means in order to increase the performance of the respective phases. Pulsed under pressure can increase the sampling yield whereas pulsed over pressure results in a more efficient ejection of the sample, i.e. less sample tissue is left in the needle. When using this pulsed regime, it is possible to directly connect the hose to a vacuum source, such as a vacuum pump or the like, in the console. In this way, one will for instance obtain under pressure much faster than using the pressure-pump device.

Even though the inventive arrangement has been described by means of a procedure for cell-sampling from a human breast lesion, the arrangement shall not be regarded as being limited to such only. The arrangement is fully functional with other kinds of lesion locations, such as for instance in the prostate, thyroid gland or lymph nodes as well as with animal patients. Moreover, the inventive arrangement may very well be used to take a sample of cells from any tissue sample site.

It will be understood that the invention is not restricted to the above-described exemplifying embodiments thereof and that several conceivable modifications of the invention are possible within the scope of the following claims.

The invention claimed is:

1. Fine needle aspiration arrangement for taking a cell sample from a suspicious human or animal tissue lesion or a tumor, comprising:
   a hollow needle (2),
   a longitudinal movement means (6) adapted to apply an oscillating longitudinal movement (10) to the needle (2),
   a rotational movement means (8) adapted to apply a rotational movement (12) to the needle (2), when the needle is positioned inside the cell sample site, and
   a pressure regulating means (14) adapted to create under pressure in the hollow part (20) of said needle for taking the cell sample,
   wherein said rotational movement (12) and said longitudinal movement (10) are maneuvered independent from each other and
   wherein said longitudinal movement (10) is in the range of 30-300 Hz,
   wherein said rotational movement (12) is adapted to be applied to the needle (2) while the needle is in the longitudinal movement (10), and
   wherein the hollow part (20) of the needle (2) is filled with a liquid that prevents unwanted tissue from entering the hollow part of the needle when the needle is inserted into the cell sample site and wherein the pressure regulating means (14) is adapted to apply reduced pressure to the hollow part (20) of said needle in order to remove the liquid from the needle (2).

2. Arrangement according to claim 1, wherein the arrangement further comprises a heat generating means (18) adapted to generate and apply energy to the needle (2) in order to heat tissue surrounding the needle.

3. Arrangement according to claim 2, wherein said heat generating means is a radio frequency energy source and the applied energy is radio frequency energy.

4. Arrangement according to claim 1, wherein the pressure regulating means is adapted to create under pressure and/or over pressure in the hollow part (20) of said needle in the form of predetermined pulses.

5. Arrangement according to claim 1, wherein the needle (2) is provided with a removable filter, and said filter collects cells from the sample.

6. Arrangement according to claim 1, wherein the arrangement further comprises control means that controls parameters of the longitudinal and rotational movement (10, 12) of the needle (2).

7. Arrangement according to claim 6, wherein said control means is provided with programming means that enables pre-programming of the parameters of the longitudinal and rotational movement (10, 12) of the needle (2).

8. Arrangement according to claim 1, wherein the arrangement further comprises a sample kit comprising the hollow needle (2), a hose (7), a coupling adapter means (21) and a pressure-pump device (9), wherein the needle is adapted to be fitted at a first end of the hose via the coupling adapter means and the pressure-pump device is adapted to be fitted at a second end of said hose, the pressure pump device being further adapted to create over and under pressure in the hollow part (20) of the needle.

9. Arrangement according to claim 1, wherein the arrangement comprises a hand-piece (25) that is adapted to be coupled to the hollow needle (2) via a needle coupling adapter means (21) adapted to transfer the movements (10,12) to the needle (2).

10. Fine needle aspiration arrangement for taking a cell sample from a suspicious human or animal tissue lesion or a tumor, comprising a hollow needle (2), a longitudinal movement means (6) adapted to apply an oscillating longitudinal movement (10) to the needle (2), a rotational movement means (8) adapted to apply a rotational movement (12) to the needle (2), when the needle is positioned inside the cell sample site, a pressure regulating means (14) adapted to create under pressure in the hollow part (20) of said needle for taking the cell sample, wherein said rotational movement (12) and said longitudinal movement (10) are maneuvered independent from each other, wherein the hollow part (20) of the needle (2) is filled with a liquid that prevents unwanted tissue from entering the hollow part of the needle when the needle is inserted into the cell sample site and wherein the pressure regulating means (14) is adapted to apply reduced pressure to the hollow part (20) of said needle in order to remove the liquid from the needle (2).

* * * * *